US009763444B2

(12) United States Patent
Meepagala et al.

(10) Patent No.: US 9,763,444 B2
(45) Date of Patent: Sep. 19, 2017

(54) COMPOSITIONS AND METHODS FOR REPELLING BLOOD-SUCKING AND BITING INSECTS, TICKS AND MITES (71) Applicant: The United States of America, as represented by the Secretary of Agriculture, Washington, DC (US)

(72) Inventors: Kumudini M. Meepagala, Oxford, MS (US); Ulrich R. Bernier, Gainesville, FL (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/051,168

(22) Filed: Feb. 23, 2016

(65) Prior Publication Data
US 2016/0165886 A1    Jun. 16, 2016

Related U.S. Application Data (62) Division of application No. 13/784,937, filed on Mar. 5, 2013, now abandoned.

(51) Int. Cl.
*A61K 31/355* (2006.01)
*A01N 43/16* (2006.01)
*C07D 311/58* (2006.01)

(52) U.S. Cl.
CPC ............ *A01N 43/16* (2013.01); *C07D 311/58* (2013.01)

(58) Field of Classification Search
CPC .............................. A01N 43/16; C07D 311/58
See application file for complete search history.

(56) References Cited

U.S. PATENT DOCUMENTS

| | | | |
|---|---|---|---|
| 4,162,326 A | 7/1979 | Mihailovski |
| 4,347,256 A | 8/1982 | Bowers |
| 4,656,189 A | 4/1987 | Bowers |
| 4,716,238 A | 12/1987 | Timar et al. |
| 4,866,089 A | 9/1989 | Timar et al. |
| 5,141,939 A | 8/1992 | Weissmuller et al. |
| 5,756,114 A | 5/1998 | Peterson |
| 6,585,991 B1 | 7/2003 | Rojas et al. |

FOREIGN PATENT DOCUMENTS

WO    WO2011-110292    9/2011

OTHER PUBLICATIONS

Meepagala et al (Pest Management Science, 2011, 67, 1446-1450).*
De La Fuenta, Gabriel et al., "Chromene Amides from Amyris Texana," Phytochemistry, 1991, vol. 30, No. 8, pp. 2677-2684, Great Britain.
Messenger, Mathew T. et al., "First Report of Incisitermes Minor (Isoptera:Kalotermitidae) in Louisiana," Florida Entomologist, Mar. 2000, vol. 83, No. 1, pp. 92-93.
Grace, J. Kenneth et al., "Termite Resistance of Wood Species Grown in Hawaii," Forest Products Journal, Oct. 1996, vol. 46, No. 10, pp. 57-60.
Scheffrahn, Rudolf H. et al., "Keys to Soldier and Winged Adult Termites (Isoptera) of Florida," Florida Entomologist, Dec. 1994, vol. 77, No. 4, pp.460-474.
Smith, Leverett R. et al., "Synthesis and Structure-Phytotoxicity Relationships of Acetylenic Phenois and Chromene Metabolites, and their Analogues, from the Grapevine pathogen *Eutypa lata*," Journal of Natural Products, 2003, vol. 56, No. 2, pp. 169-176.
Lu, Yinrong et al., "Flavonoid and phenolic gycosides and Salvia officinalis ," Phytochemistry, 2000, vol. 55, pp. 263-267.
Lax, Alan R. et al., "Targeted management of Formosan subterran termite Coptotermes Formosanus Shiraki (Isoptera:Rhinotermitidae)," Pest Management Science, 2003, vol. 59, pp. 788-800.
Woodson, W.D. et al., "Current Distributionof the Formosan Subterranean Termite (Isoptera:Rhinotermitidae) in the United States," Sociobiology, 2001, vol. 37, No. 38,pp. 661-671.
Henderson, G. et al., "Keeping Formosan Termites away from underground telephone lines," Louisiana Agriculture, Winter 1999, vol. 42, No. 1, pp. 5-6.
Aida, Y. et al., Effects of Chroman Derivative on Platelet Aggregation Induced by some Aggregating Agents in Rabbits, Clinical and Experimental Pharmacology and Physiology, 1998, 25(11), 939-944.
Hiyashi et al., Development of 4-Alkylphenyl Aralkyl Ethers and Related Compounds as Potent Insect Juvenile -Hormone Mimetics and Structural Aspects of Their Activity, Journal of Agricultural and Food Chemistry, 1990, 38, 1965-1971.
Katrizky and Rees, Comprehensive Heterocyclic Chemistry, vol. 3, Pergamon: 1984, pp. 742-744.
Fagoonee, I. et al., Anti-Gonadotrophic Hormones from the Goatweed, *Ageratum conzyzoides*, Insect Sci. Application, 1981, vol. 1(4), pp. 373-376.
Wisdom, C.S. et al., Toxicity and Deterrency of Sesquiterpene Lactones and Chromenes to the Corn Earworm (Lepidoptera: Noctuidae), J. Econ. Entomol., 1983, vol. 76, pp. 993-998.
Proksch, P. et al., Phototoxic and Insecticidal Activities of Chromenes and Benzofurans from Encelia, Journal of Natural Products, 1983, vol. 46(3), pp. 331-334.
Isman, M.B. et al., Toxicity of Natural Chromene Derivatives to a Grasshopper, Naturwissenschaften, 1986, vol. 73, pp. 500-501.

(Continued)

*Primary Examiner* — Jason Sims
*Assistant Examiner* — Ibrahim D Bori
(74) *Attorney, Agent, or Firm* — John D. Fado; G. Byron Stover (57) ABSTRACT

Chromene derivatives based on a chromene amide isolated from *Amyris texana*. Also disclosed are compositions containing chromene derivatives (synthetic or natural) based on a chromene amide isolated from *Amyris texana*. Also methods for repelling blood-sucking and biting insects, ticks and mites involving treating (or exposing) an object (e.g., mammals such as humans) or area (e.g., a surface such as human skin) with a blood-sucking and biting insects, ticks and mites repelling effective amount of at least one compound selected from chromene derivatives (synthetic or natural) based on a chromene amide isolated from *Amyris texana*.

4 Claims, 2 Drawing Sheets

(56) References Cited

OTHER PUBLICATIONS

Gundidza, M., Insecticidal Activity of Monadenium lugardae Latex, Planta Med., 1986, vol. 6, p. 558.

Meepagala, K.M. et al., New Class of Algicidal Compounds and Fungicidal Activities Derived from a Chromene Amide of Amyris texana, J. Agric. Food Chem., 2010, vol. 58, pp. 9476-9482.

Badal, S. et al., Cytochrome P450 1 enzyme inhibition and anticancer potential of chromene amides from Amyris plumieri, Fitoterapia, 2011, vol. 82, pp. 230-236.

Stevers, C.V. et al., Insect Repellent/ Antifeedant Activity of 2,4-Methanoproline and Derivatives agaínsr a Leaf-and Seed-Feeding Pest Insect, J. Agric. Food Chem., 2005, vol. 53, pp. 1945-1948.

Pohlit, A.M. et al., Patent Literature on Mosquito Repellent Inventions which Contain Plant Essential Oils—A Review, Planta Med., 2011, vol. 77, pp. 598-617.

Agarwal, S.K. et al., Antifertility chromene from Blepharispermum subsessile, Fitoterapia, 1999, vol. 70, pp. 435-437.

Meepagala et al.: "Larvicidal and Adulticidal Activity of Chroman and Chromene Analogues against Susceptible and Permethrin-Resistant Mosquito Strains", Journal of Agricultural and Food Chemistry (2016), 64(24), 4914-4920.

Meepagala et al., "Mosquito Repellents Based on a Natural Chromene Analogue with Longer Duration of Action than N,N-Diethyl-meta-toluamide (DEET)", Journal of Agricultural and Food Chemistry (2013), 61(39), 9293-9297.

* cited by examiner

Figure 1

(2) $R_1$=CH$_2$OH
$R_2, R_3, R_4$= H (3) $R_1$=OH
$R_3, R_4$= H
$R_2$= C(O)CH$_3$ (4) $R_1$=OMe
$R_2, R_3$= H
$R_4$=CH$_2$OH (5) $R_1, R_3, R_4$= H
$R_2$=C(O)OCH$_3$ (6) $R_1$=C(O)OCH$_3$
$R_2, R_3, R_4$= H (7) $R_2$= CH$_2$OH
$R_1, R_3, R_4$=H (8) $R_3$= C(O)OCH$_3$
$R_1, R_2, R_4$=H (9) $R_2$=CH$_2$CH$_2$OH
$R_1, R_3, R_4$= H (10) $R_2$= CH$_2$C(O)OCH$_3$
$R_1, R_3, R_4$=H (11) $R_1$=CH$_2$OH
$R_2, R_3$= H
$R_4$= Cl (12) $R_3$=Cl
$R_1, R_2, R_4$= H (13) $R_1$=COOH
$R_2, R_3$= H
$R_4$=Cl (14) $R_1$=C(O)OCH$_3$
$R_2, R_3$= H
$R_4$=Cl (15) $R_4$=Cl
$R_1, R_2, R_3$= H (16) $R_1$=C(O)OCH$_3$
$R_3, R_4$= H
$R_2$=Cl (17) $R_2$=Cl
$R_1, R_3, R_4$= H (18) $R_1$=CH$_2$OCH$_3$
$R_2, R_3, R_4$= H (19) $R_2$=CH$_2$CH$_2$OCH$_3$
$R_1, R_3, R_4$= H

Figure 2

COMPOSITIONS AND METHODS FOR REPELLING BLOOD-SUCKING AND BITING INSECTS, TICKS AND MITES

This is a divisional of application Ser. No. 13/784,937, filed 5 Mar. 2013, which is herein incorporated by reference in its entirety.

BACKGROUND OF THE INVENTION

Disclosed are chromene derivatives based on a chromene amide isolated from *Amyris texana*. Also disclosed are compositions containing chromene derivatives (synthetic or natural) based on a chromene amide isolated from *Amyris texana*. Furthermore there are provided methods for repelling blood-sucking and biting insects, ticks and mites involving treating (or exposing) an object (e.g., mammals such as humans) or area (e.g., a surface such as human skin) with a blood-sucking and biting insects, ticks and mites repelling effective amount of at least one compound selected from chromene derivatives (synthetic or natural) based on a chromene amide isolated from *Amyris texana*.

Dengue fever and yellow fever are caused by arboviruses which are transmitted by female mosquitoes belonging to the genus *Aedes*, particularly *Ae. aegypti*. Symptoms of dengue infection in humans include headache, fever, exhaustion, severe muscle and joint pain, swollen glands (lymphadenopathy), and rash. Other symptoms include bleeding gums, severe pain behind the eyes, and red palms and soles. The more severe form of this viral illness is dengue viral hemorrhagic fever which includes headache, fever, rash, and evidence of hemorrhage in the body. This form of dengue fever is life threatening and can progress to dengue shock syndrome, the most severe stage of the illness (Dengue Hemorrhagic Fever: Diagnosis, Treatment, Prevention and Control, 2nd Ed., Geneva, World Health Organization, 1997, pages 1-83).

After an individual receives a mosquito bite where saliva is injected from an infected mosquito, the incubation period ranges from three to eight days before the signs and symptoms of dengue appear. The temperature of the body rises quickly, as high as 40° C. with low heart rate (bradycardia) and low blood pressure (hypotension). Although there is a vaccine for yellow fever, there is no specific treatment or vaccine for dengue. The only way to prevent dengue virus transmission is to prevent bites from the disease-carrying mosquitoes by eliminating them. Application of insecticide is one of the major control methods for this medically important insect pest. However, few new insecticides have been developed for mosquito control and recently the most popular repellent, DEET, was reported as a neurotoxin (Corbel, V., et al., BMC Biology, 7:47 (2009)). New mosquito repellents without this potential side effect are thus desired.

We have identified some natural product-derived compounds that have higher duration of repellent action and potency against insects such as mosquitoes than DEET.

SUMMARY OF THE INVENTION

Disclosed are chromene derivatives based on a chromene amide isolated from *Amyris texana*. Also disclosed are compositions containing chromene derivatives (synthetic or natural) based on a chromene amide isolated from *Amyris texana*. Furthermore there are provided methods for repelling blood-sucking and biting insects, ticks and mites involving treating (or exposing) an object (e.g., mammals such as humans) or area (e.g., a surface such as human skin) with a blood-sucking and biting insects, ticks and mites repelling effective amount of at least one compound selected from chromene derivatives (synthetic or natural) based on a chromene amide isolated from *Amyris texana*.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Disclosed are chromene derivatives based on a chromene amide isolated from *Amyris texana*. Also disclosed are compositions containing chromene derivatives (synthetic or natural) based on a chromene amide isolated from *Amyris texana*. Also disclosed are methods for repelling blood-sucking and biting insects, ticks and mites, involving treating (or exposing) an object (e.g., mammals such as humans) or area (e.g., a surface such as human skin) with a blood-sucking and biting insects, ticks and mites repelling effective amount of at least one compound selected from where (2) $R_1$=$CH_2OH$ and $R_2$, $R_3$, $R_4$=H; (3) where R=OH, $R_2$=$C(O)CH_3$ and $R_3$, $R_4$=H; (4) where $R_1$=OMe, $R_2$ and $R_3$=H, and $R_4$=$CH_2OH$; (5) where $R_1$, $R_3$, and $R_4$=H and $R_2$=$C(O)OCH_3$; (6) where $R_2$, $R_3$, and $R_4$=H and $R_1$=$C(O)OCH_3$; (7) where $R_1$, $R_3$, and $R_4$=H and $R_2$=$CH_2OH$; (8) where $R_1$, $R_2$, and $R_4$=H and $R_3$=$C(O)OCH_3$; (9) where $R_2$=$CH_2CH_2OH$ and $R_1$, $R_3$, and $R_4$=H; (10) where $R_2$=$CH_2C(O)OCH_3$ and $R_1$, $R_3$, and $R_4$=H; (11) where $R_1$=$CH_2OH$, $R_2$ and $R_3$=H, and $R_4$=Cl; (12) where $R_1$, $R_2$, and $R_4$=H and $R_3$=Cl; (13) where $R_1$=COOH, $R_2$ and $R_3$=H, and $R_4$=Cl; (14) where $R_1$=$C(O)OCH_3$, $R_2$ and $R_3$=H, and $R_4$=Cl; (15) where $R_1$, $R_2$ and $R_3$=H and $R_4$=Cl; (16) where $R_1$=$C(O)OCH_3$, $R_3$ and $R_4$=H, and $R_2$=Cl; (17) where $R_1$, $R_3$ and $R_4$=H and $R_2$=Cl; (18) where $R_1$=$CH_2OCH_3$, $R_2$, $R_3$ and $R_4$=H; (19) where $R_2$=$CH_2CH_2OCH_3$ and $R_1$, $R_3$ and $R_4$=H; and mixtures thereof, and optionally a carrier or carrier material. Preferably where (2) $R_1=CH_2OH$ and $R_2$, $R_3$, $R_4=H$ and/or (11) where $R_1=CH_2OH$, $R_2$ and $R_3=H$, and $R_4=Cl$.

The terms "object" or "area" as used herein include any place where the presence of target pests (e.g., mosquitoes) is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of a living being, such as skin, fur, hair, or clothing. Thus the method includes dispensing the compounds described herein into the environment in vapor form (e.g., an aerosol) preferably using devices that allow a slow sustained release of these compounds into the environment from a sealed canister.

The compositions and compounds can also be used for repelling harmful or troublesome blood-sucking and biting insects, ticks and mites including mosquitoes (for example *Aedes, Culex* and *Anopheles* species including but not limited to Tiger mosquitoes, *Aedes aboriginis, Aedes aegypti, Aedes albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefasciatus*), sand flies (for example *Phlebotomus* and *Lutzomyia* species), bed bugs (for example *Cimex lectularius*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyla chloropyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example *Melaphagus orinus*), and fleas (for example *Pulex irritans, Cthenocephalides canis* and *Xenopsylla cheopis*), sand fleas (for example *Dermatophilus penetrans*), and blood-feeding ticks include (for example, *Ornithodorus moubata, Ixodes ricinus, Ixodes scapularis, Boophilus microplus, Amblyomma americanum,* and *Amblyomma hebreum.*, and mites include, for example, *Sarcoptes scabiei* and *Dermanyssus gallinae*).

The compounds, which can be used in undiluted or diluted form, can be converted into formulations customary for repellents. They can be used in all the presentation forms customary in cosmetics and public health pesticides, for example in the form of solutions, emulsions, gels, ointments, pastes, creams, powders, sticks, sprays or aerosols from spray cans.

For use in the non-cosmetic sector, the compounds can be incorporated, for example, into granules, oily spraying agents or slow release formulations.

The formulations are prepared in a known manner by mixing or diluting the compounds with solvents (for example xylene, chlorobenzenes, paraffins, methanol, ethanol, isopropanol or water), carriers (for example kaolins, aluminas, talc, chalk, highly disperse silicic acid and silicates, nanoclays), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The compounds can be mixed with one another in the formulations or can also be used as mixtures with other known active compounds (for example sunscreen agents). The formulations in general contain between about 0.1 and about 95% (e.g., 0.1-95%) by weight of active compound, preferably between about 0.5 and about 90% (e.g., 0.5-90%).

For protection from mosquitoes, the compounds are generally either applied to human or animal skin, or items of clothing and other objects are treated with the compounds. Preferably, the compounds are dispensed into the environment (e.g., outdoors or indoors) in vapor form (e.g., an aerosol).

The compounds are also suitable as an additive to impregnating agents, for example, textile webs, articles of clothing and packaging materials, and as an additive to polishing, cleaning and window-cleaning agents.

The compositions contain a carrier and the compound. The repellent is generally applied with a carrier component. The carrier component can be a liquid or a solid material. As is known in the art, the vehicle or carrier to be used refers to a substrate such as a gel, polymers, or the like. All of these substrates have been used to release insect repellents and are well known in the art. The carrier or carrier material as used herein is defined as not including a plant (e.g., *Amyris texana*) or the extract from which a compound is isolated.

The compounds herein are described as repellents because they result in a reduction in the ability of mosquitoes to locate a host, and thus reduce the incidence of biting. Generally, an insect repellant is any compound or composition which deters insects from a host, thus the term "repelling" is defined as causing insects (e.g., *Aedes aegypti*) to make oriented movements away from a source of a chemical repellent (Dethier, V. L., et al., J. Econ. Ent., 53: 134-136 (1960)) but also includes inhibiting feeding by mosquitoes when a chemical is present in a place where mosquitoes would, in the absence of the chemical, feed. Thus the term "repelling" also includes reducing the number of insect (e.g., *Aedes aegypti*) bites on a treated area or object (e.g., mammalian skin which has been treated topically with the compositions or compounds) when compared to the same area or object which is untreated.

The amount of the compound used will be at least an effective amount. The term "effective amount," as used herein, means the minimum amount of the compound needed to reduce the ability of mosquitoes to locate a host and thus reduce the incidence of biting, or to cause mosquitoes to make oriented movements away from a treated area or object (e.g., mammalian skin which has been treated topically with the compound) when compared to the same area or object which is untreated. The term "effective amount," as used herein, also means the minimum amount of the compound needed to reduce the number of insect (e.g., *Aedes aegypti*) bites on a treated area or object (e.g., mammalian skin which has been treated topically with the compound) when compared to the same area or object which is untreated. Effective concentrations of the compound in the compositions may vary between about 0.1 and about 95% (e.g., 0.1-95%) by weight, preferably between about 0.5 and about 90% (e.g., 0.5-90%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

The compounds may be used with other repellents or mosquitoe control agents (e.g., insecticides, chemosterilants or the like). When used, these agents should be used in an amount which, as readily determined by one skilled in the arts, will not interfere with the effectiveness of the compound.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

General Experimental Procedures: Extracts were analyzed on silica gel TLC plates GF with fluorescent indicator (250 micron, Analtech, Newark, Del.). Iodine vapor, UV light (at 254 and 365 nm), and Dragendorff and anisaldehyde spray reagents were used for the detection of compounds. Column chromatography was carried out with kieselgel 60 (particle size 0.063-0.2 mm, Merck) with mixtures of hexane and acetone in varying amounts. All solvents were reagent grade and used without further purification. $^1$H and $^{13}$C NMR spectra were recorded either on a Bruker AMX NMR spectrometer operating at 400 MHz for $^1$H NMR and at 100 MHz for $^{13}$C NMR or on a Varian Mercury AS400 spectrometer operating at 400 MHz for $^1$H NMR and at 100 MHz for $^{13}$C NMR. The HR-ESIMS was measured using a Bruker QTOF micromass spectrometer or using Jeol ACCU TOF JMS-T1000 mass spectrometer. GC-MS analysis was carried out on an HP5790 MSD spectrometer (Hewlett Packard, USA) equipped with GC 5890 using a DB-1 column (20 m×0.2 mm, 0.18 μm film thickness). The oven was temperature programmed from 60° C. (5 min) to 280° C. (20 min) at 5° C./min with helium as the carrier gas.

Plant material: Leaves of *Amyris texana* were collected in Cameron County in South Texas in June. A voucher specimen (BUR 190204 a) was deposited at the University of Mississippi herbarium. The leaves were air-dried, ground, and stored at room temperature until they were extracted.

Extraction and fractionation: Extraction and isolation of N-[2-(2,2-Dimethyl-2H-chromen-6-yl)-ethyl]-3,N-dimethyl-butyramide, chromene amide (1) was done according to previously published methods (Meepagala, K. M., et al., J. Agric. Food Chem., 58(17): 9476-9482 (2010)).

Figure 1:
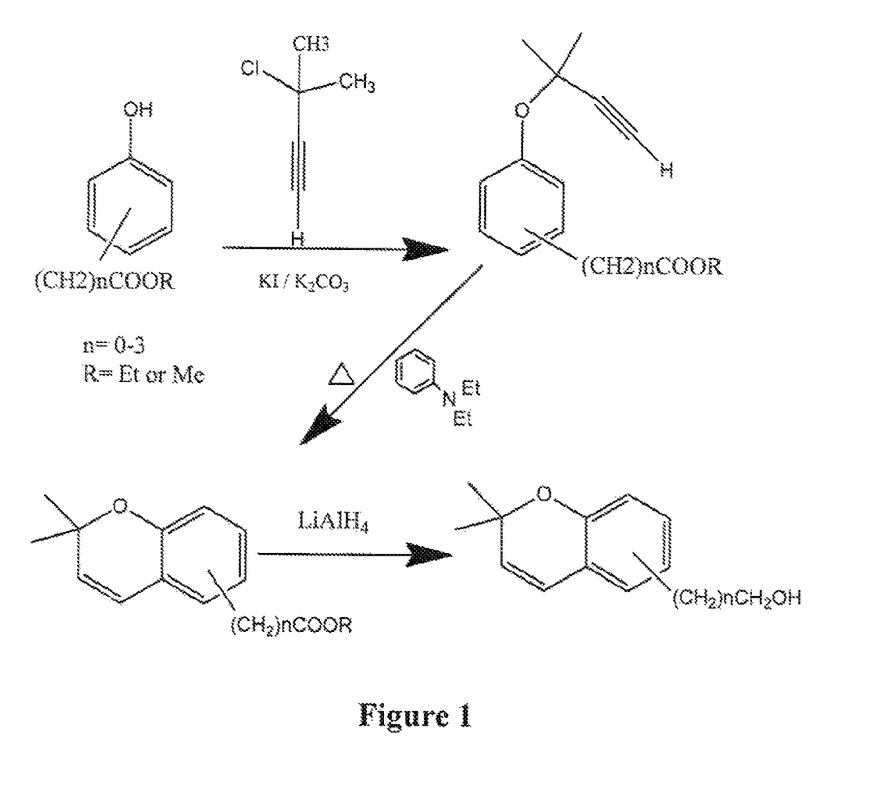
FIG. 1 shows a general synthetic procedure of chromene analogs as described below.

Syntheses of analogs: The general synthetic procedure involved reaction of the appropriate phenol with 3-chloro-3-methyl-1-butyne followed by pyran ring formation by heating with N,N diethylaniline (FIG. 1). Compounds (2-19) (FIG. 2) were synthesized and identified using spectroscopic data according to published methods (De la Fuente, G., et al., Phytochemistry, 30: 2677-284 (1991); Wattanapiromsakul, C., and P. G. Waterman, Phytochemistry, 55: 269-273 (2000); Meepagala, K. M., et al., J. Agric. Food Chem., 58(17): 9476-9482 (2010); Smith, L. R., et al., J. of Nat. Prod., 66: 169-176 (2003); Meepagala, K. M., et al., Pest Management Science, doi: 10.1002/ps.2196).

5-(methoxymethyl)-2,2-dimethyl-2H-chromene (18): To 2 (1.9 g, 0.01 moles) under $N_2$ in dry THF (50 mL) was added methyl iodide (5.6 g, 0.04 moles) followed by NaH (60 g, 1.5 moles, 60% dispersion in mineral oil). The reaction mixture was stirred for 12 hr at 80° C. The solvent was evaporated, the residue was partioned between water (100 mL) and diethyl ether (100 ml) and the ether layer was dried over anhydrous $Na_2SO_4$ and the solvent was evaporated to afford a pale yellow oil which was purified by silica gel column chromatography using 5% EtOAc in hexane to afford (18) (yield, 1.7 g, 0.0083 mol, 83%). $^1$H NMR (CDCl$_3$) δ 1.41 (6H, s), 3.34 (3H, s), 4.44 (2H, s), 5.64 (1H, d, J=12 Hz), 6.58 (1H, d, J=8 Hz), 6.75 (1H, d, J=8 Hz), 6.81 (1H, d, J=8 Hz), 7.05 (1H, t, J=8 Hz); 13C NMR (CDCl$_3$) δ 27.82, 57.87, 72.25, 116.61, 118.95, 119.90, 127.71, 128.41, 131.03, 133.37, 153.15; HRMS (ESI-TOF) m/z 203.09436 [M–H]– (calcd for $C_{13}H_{15}O_2$, 203.10720).

6-(2-methoxyethyl)-2,2-dimethyl-2H-chromene (19): To (9) (2.04 g, 0.01 moles) under $N_2$ in dry THF (50 mL) was added methyl iodide (5.6 g, 0.04 moles) followed by NaH (60 g, 1.5 moles, 60% dispersion in mineral oil). The reaction mixture was stirred for 12 hr at 80° C. The solvent was evaporated to afford a pale yellow oil which was partitioned between water (100 mL) and diethyl ether (100 ml) and the ether layer was dried over anhydrous $Na_2SO_4$ and the solvent was evaporated to afford a pale yellow oil. This oil was purified by silica gel column chromatography using 5% EtOAc in hexane to afford (19) (yield, 1.9 g, 0.0088 mol, 87%). $^1$H NMR (CDCl$_3$) δ 1.41 (6H, s), 2.77 (2H, t, J=8 Hz), 3.34 (3H, s), 3.55 (2H, t, J=8 Hz), 5.58 (1H, d, J=8 Hz) 6.69 (1H, d, J=8 Hz), 6.82 (1H, d, J=1.7 Hz), 6.69 (1H, d, J=8 Hz), 6.82 (1H, d, H=2 Hz), 6.94 (1H, dd, J=8 Hz, 2 Hz); 13C NMR (CDCl$_3$) δ 27.96, 35.35, 53.43, 58.63, 73.85, 76.01, 116.12, 121.08, 122.32, 129.28, 130.77, 130.98, 151.30; HRMS (ESI-TOF) m/z 217.122848. [M–H]– (calcd for $C_{14}H_{17}O_2$, 217.122855).

4-chloro-3-hydroxymethylbenzoate (20): 4-chloro-3-hydroxymethylbenzoic acid (8.6 g, 50 mmol) was dissolved in methanol (120 mL), and the solution was placed under nitrogen and cooled in an ice bath. Acetyl chloride (7 mL, 100 mmol) was added via syringe. The reaction mixture was then heated to reflux in an oil bath for 8 h. Methanol was removed and the resulting solid was dissolved in water (75 mL) and extracted with ethyl acetate (3×1000 mL). The combined ethyl acetate layers were dried with $Na_2SO_4$ and concentrated. 4-chloro-3-hydroxymethylbenzoate was purified by flash column chromatography using 10-30% ethyl acetate in hexane to afford pale yellow solid (8.4 g, 90% yield). Identity was confirmed by comparison of spectroscopic data with those published in the literature (Journal of Medicinal Chemistry, 49(25) 7413-7426 (2006)).

Methyl 8-chloro-2,2-dimethyl-2H-chromene-5-carboxylate (14): 4-chloro-3-hydroxymethylbenzoate (20) (5.1 g, 27.6 mmol) was refluxed under $N_2$ with a mixture of KI (6 g), anhy. $K_2CO_3$ (6 g), and 3-chloro-3-methyl-1-butyne (6.8 mL, 60.5 mmol) in acetone (30 mL) for 48 hrs. The mixture was allowed to cool to room temperature, filtered and the residue was washed with acetone. The combined acetone solution was evaporated to afford a gum which showed a single major spot on TLC (eluted in 5% ethyl acetate in hexane). This gum was refluxed with N,N,-diethylaniline (35 mL) under $N_2$ with stirring (200-210° C.) for 1 hr. The reaction mixture was allowed to cool to room temperature and diluted with ethyl acetate (300 mL). The ethyl acetate solution was washed with 6M aqueous HCl (100 mL×2)

followed by saturated aqueous NaCl, and dried over anhydrous $Na_2SO_4$. Ethyl acetate was removed under reduced pressure to afford a pale yellow oil which was purified by silica gel column chromatography using 5% acetone in hexane to afford (14) as white crystals (4.9 g, 71% yield). $^1H$ NMR ($CDCl_3$) δ 1.48 (61H, s), 3.88 (3H, s), 5.81 (1H, d, J=10.4 Hz), 7.21 (1H, d, J=8 Hz), 7.28 (1H, d, J=10.4 Hz), 7.41 (1H, d, J=8 Hz). HRMS (ESI-TOF) m/z 253.063152 $[M+H]^+$ (calcd for $C_{13}H_{14}ClO_3$, 253.063148).

(8-chloro-2,2-dimethyl-2H-chromen-5-yl)methanol (11): To an ice cold solution of 14 (2 g, 7.9 mmol) in anhydrous diethyl ether (75 mL) $LiAlH_4$ (500 mg) was added and then refluxed for 15 min under $N_2$. Excess $LiAlH_4$ was destroyed by adding ethyl acetate (20 mL). The reaction mixture was cooled in ice, 20% NaOH (5 mL) was added with stirring. The organic layer was decanted, residue was washed with diethyl ether (2×100 mL) and the combined ether layer was dried over anhydrous $MgSO_4$ and evaporated under reduced pressure to afford (11) a clear colorless oil (1.7 g, 7.5 mmol, 94%). $^1H$ NMR ($CDCl_3$) δ 1.47 (6H, s), 4.63 (2H, s), 5.73 (1H, d, J 8 Hz), 6.57 (1H, d, J=12 Hz), 6.78 (1H, d, J=8 Hz), 7.14 (1H, d, J=8 Hz). HRMS (ESI-TOF) m/z 225.068257 $[M+H]^+$ (calcd for $C_{12}H_{14}ClO_2$, 225.068233).

8-chloro-2,2-dimethyl-2H-chromene-5-carboxylic acid (13): To (2.0 g, 7.9 mmol) in methanol (30 mL) was added 10% NaOH in water (10 mL) and stirred at room temperature for 12 h. Methanol was evaporated, NaOH was neutralized by adding cold IN HCl in excess and extracted with ethyl acetate (100×2 mL). The combined ethyl acetate extract was dried over anhydrous $Na_2SO_4$ and the solvent was evaporated under reduced pressure to obtain 13 as a white solid. This solid was crystallized with ethyl acetate in hexane to obtain white crystals (1.6 g, 85% yield). $^1H$ NMR ($CDCl_3$) δ 1.49 (6H, s), 5.85 (1H, d, J=10 Hz), 7.26 (1H, d, J=3.6 Hz), 7.37 (1H, d, J=10 Hz), 7.56 (1H, d, J=8 Hz). HRMS (ESI-TOF) m/z 237.031837 $[M-H]^-$ (calcd for $C_{12}H_{10}ClO_3$, 237.031848).

Bioassay for mosquito repellent activity: Repellency screening test for experimental chemicals were carried out to identify candidates that might be useful repellents. The repellent efficacy was compared to that of the standard repellent, DEET. Experimental compounds were assessed in one of two ways: (1) a range of concentration was evaluated to determine the minimum effective dosage (MED) which was the concentration threshold of where the repellent began to fail and allowed bites, or (2) a predetermined concentration of each repellent was applied to cloth and the activity was evaluated over several days (or in some cases months) (Katritzky, A. R., et al., Proc. Nat. Acad. Sci. (US), 105, 7359-7364 (2008); Katritzky, A. R., et al., Journal of Med. Entomol., 47: 924-938 (2010)). When conducting assays for repellency, a failure point was also predetermined for those measurements. Since experiments described herein used about 500 female mosquitoes per test, the failure point was set at 1% (equal to 5 bites) received during a test interval. From 3 to 5 volunteers participated in the screening of each set of chemicals.

Minimum Effective Dosage (MED) Test: The MED bioassays on treated cloth were a method of screening to determine the minimum amount of a repellent needed to prevent bites. Experimental compounds were prepared in solution by combining 0.15 g of experimental chemical with 2 mL of acetone in a 7.1 mL screwtop glass vial. This solution was then serially diluted to obtain nine concentrations when applied on to the cloth patch: 1.5, 0.75, 0.375, 0.187, 0.094, 0.047, 0.023, 0.011, and 0.006 $mg/cm^2$. The standard N,N-diethyl-3-methylbenzamide (DEET) was also tested at the same concentration levels to serve as a control and a comparison for relative repellency. A 50 $cm^2$ (5 cm×10 cm) patch of muslin cloth was rolled lengthwise and placed into each of the glass vials and sealed with a screwtop so it soaked up the solution. Just prior to the experiment, the pieces of treated cloth were removed from the vials, affixed to card stock tabs (5 cm×3 cm) with staples, and hung with masking tape on a rack to dry and allow acetone to evaporate. Volunteers wore a latex glove over their hands, a nylon stocking over their arm, and then wrapped a plastic Velcro-sealed sleeve over their entire forearm with a 32 $cm^2$ (4 cm×8 cm) window cut-out to allow mosquitoes to bite through. The nylon stocking acted as a barrier between the dried cloth and the skin, an additional precaution with experimental compounds. Dried cloth patches were stretched across the window in the plastic sleeve and held in place with masking tape. Volunteers placed their sleeve-covered arms into a screened cage for a one minute period with approximately 500 female *Ae. aegypti* mosquitoes that had been preselected for host-seeking behavior using a draw box (Posey, K. H., and C. E. Schreck, Mosquito News, 41: 566-568 (1981)). A cloth patch receiving a 1% bite through level, or 5 mosquito bites within 1 minute, resulted in a failure of the compound to repel whereas a cloth patch receiving 0-4 bites within a minute was a passing result. The MED recorded was the lowest passing concentration level tested for the experimental compound. These results from all the volunteers were averaged for each experimental compound and reported as the mean MED. All human volunteers in the study provided informed consent to participate of a protocol approved by the University of Florida Human Use Institutional Review Board (IRB #636-2005).

Complete Protection Time Test: Complete protection time (CPT) on treated cloth is a method of screening that is used to determine the repellent duration for experimental chemicals that have not been examined for safe use on humans. The standard repellent DEET was used as a positive control as a benchmark by which to compare the repellents. Experimental compounds were prepared in solution by combining 0.075 g of experimental chemical with 1 mL of acetone in a 7.1-mL screwtop glass vial. The same concentration level of DEET was also prepared in this way to serve as a control and a comparison for relative repellency. A 50 $cm^2$ (5 cm×10 cm) patch of muslin cloth was rolled lengthwise and placed into each of the glass vials and sealed with a screwtop so it soaked up the solution. Just prior to the experiment, the pieces of treated cloth were removed from the vials, affixed to card stock tabs (5 cm×3 cm) with staples, and hung with masking tape on a rack to dry and allowed the volatile acetone to evaporate. Similar to the MED tests, volunteers wore a latex glove over their hands, a nylon stocking over their arm, and then wrapped a plastic Velcro-sealed sleeve over their entire forearm with a 32 $cm^2$ (4 cm×8 cm) window cut-out to allow mosquitoes to bite through. Dried cloth patches were stretched across the window in the plastic sleeve and held in place with masking tape. Volunteers placed their sleeve-covered arms into a screened cage for a one minute period with approximately 500 female *Ae. aegypti* mosquitoes that had been preselected for host-seeking behavior using a draw box. A cloth patch that received a 1% bite through level, equal to 5 mosquitoes that bit out of 500 mosquitoes, was considered a failure at that concentration. If 0-4 bites were received, then the treated cloth was still considered to be repellent at that concentration. The duration was recorded as the number of days an experimental chemical received a passing result, with day 0 being the day the sample was first dried. These results from all the volunteers were averaged for each experimental compound and reported as the average duration of repellency. As with the tests conducted to determine CPT, volunteers in the study provided informed consent (IRB protocol #636-2005). The protocol was approved by the University of Florida Human Use Institutional Review Board.

Figure 2:
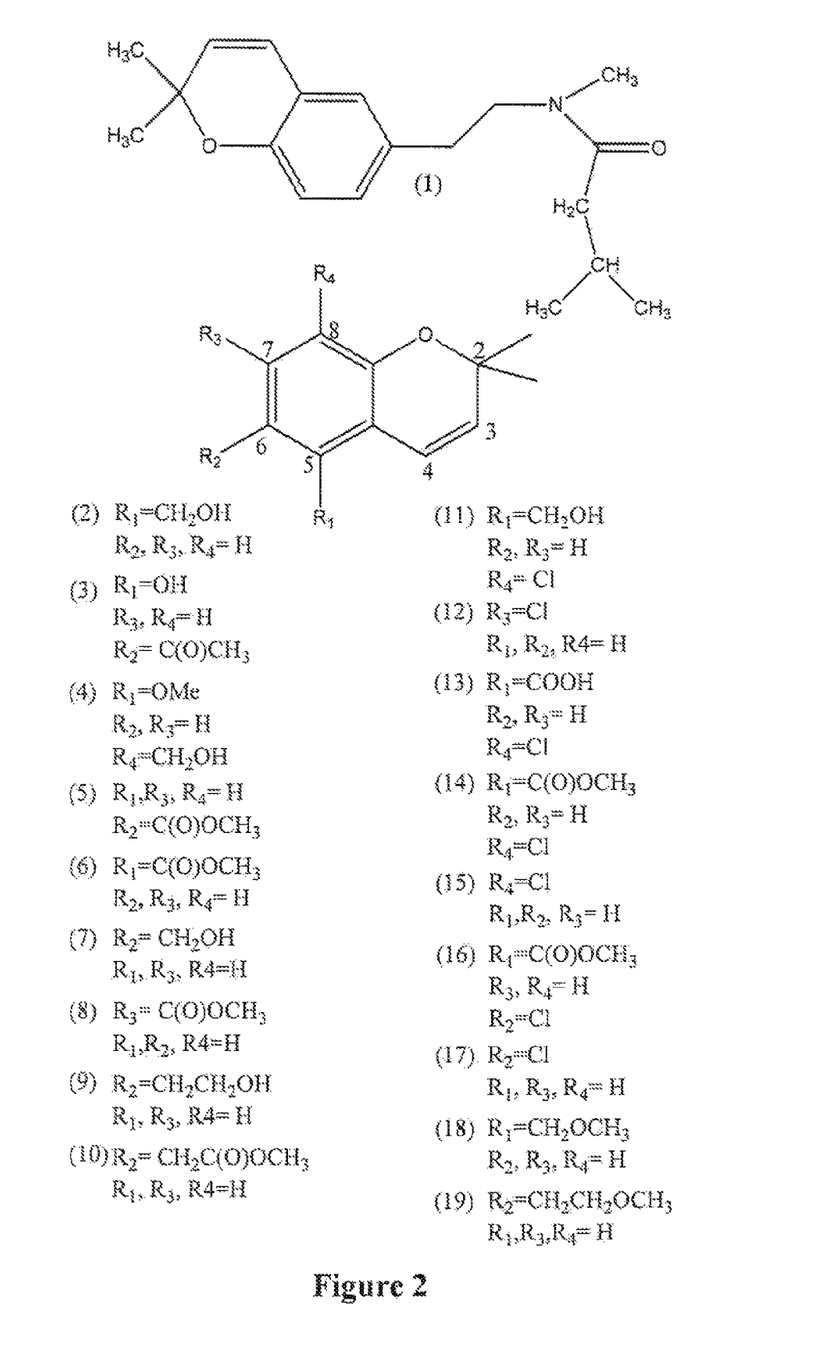
FIG. 2 shows structures of chromene analogs synthesized and tested as described below.

Results and discussion: Chromene amide (1) was isolated from the ethyl acetate extract of the leaves of *A. texana* (FIG. 1). A series of chromene derivatives were synthesized as shown in FIG. 2 and tested for mosquito repellent activity (Tables 1-5). In the preliminary assay for the MED (Table 1), the chromene analog 2 (MED 0.035 mg/cm$^2$) surprisingly showed comparable level of activity to that of DEET (MED 0.021 mg/cm$^2$). The control, acetone, was not repellent. Compound 3 with an OH group at C-5 and a COCH$_3$ group at C-6 was surprisingly the least repellent because four of 5 volunteers found it not repellent at the highest concentration tested (1.500 mg/cm$^2$). Compound 4 with an OMe group at C-5 and a CH$_2$OH group at C-8 and 5 with an acetate group at C-6 surprisingly had mixed results where the highest concentration was not repellent for some of the volunteers. Based on these initial data, more analogs were synthesized and tested (Table 2). The acetate analog of 2, 6, was surprisingly ineffective at the highest dosage tested. Similarly, 7 and 8, the regio-isomers of 2 and 5 respectively were surprisingly ineffective, suggesting that the position of CH$_2$OH was critical for the activity. Compounds 9 and 10, analogs of 7 and 8 with an additional CH$_2$ group, were less active but still surprisingly exhibited some repellency, MED 0.375 mg/cm2 and 0.500 mg/cm2, respectively. Compound 11, an analog of 2 with a Cl attached to C-8, surprisingly showed high activity with a average MED value of 0.011 mg/cm2. The other chlorinated analogs, 12 through 17, were surprisingly less active. When the active compounds were tested for duration of protection, 2 surprisingly performed best with 6 days of protection whereas 11 and DEET had 2 days of protection against *Ae. egypti* mosquitoes (Table 3). These data suggested that 2 surprisingly had the best activity and the longest duration of protection. When tested against the mosquito species *Anopheles albimanus*, these compounds were less active than DEET as repellents (Table 4). The methylated analog of 2, 18, surprisingly showed diminished repellent activity, further suggesting the importance of the CH$_2$OH group of 2 for the activity. Similarly, 19, the methylated analog of 9, surprisingly did not show any improvement of activity.

Compound 2 was also evaluated with DEET for synergistic activity. Test samples were prepared at varying molar ratios of DEET: 2 (1:0-1:8 and 0:1-0:8) and the MED values were evaluated (Table 6). These results indicated that the compound mixture did not show synergism at the ratios that were tested.

We have previously shown that chromene analogs possess termiticide activity and algecide activity (Meepagala, K. M., et al., J. Agric. Food Chem., 58(17): 9476-9482 (2010); Meepagala, K. M., 2011, Pest Management Science. doi: 10.1002/ps.2196). There are reports of chromene analogs as insecticides against specific insects: first instar of the milkweed bug *Oncopelrus fasciatus* (Proksch, P., et al., J. Nat. Prod., 46(3): 331-4 (1983); the variegated cutworm (*Peridroma saucia*, Noctuidae) and the migratory grasshopper (*Melanoplus sanguinipes*, Acrididae) (Isman, M. B., and P. Proksch, Planta Med., 52(6): 558 (1986); Isman, M. B., et al., Naturwissenschaften, 73(8): 500-1 (1986)); cotton stainer bugs (*Dysdercus flavidus*) (Fagoonee, I., and G. Umrit, Insect Sci. Appl., 1(4): 373-6 (1981); and corn earworm (*Heliothis zea* (Boddie)(Wisdom, C. S., et al., J. of Econ. Entomol., 76(5): 993-8 (1983)). To our knowledge this is the first report of chromene analogs as mosquito repellents.

In our lab we have also demonstrated that the mosquito repellent chromenes were not insecticidal on topical application to mosquitoes (Table 7). The minimum effective dosage (MED) for repellency of 99% of mosquitoes was determined by wearing treated muslin cloth with varying concentrations of the chemical. At a surface concentration of 0.011 mg/cm$^2$, nearly all mosquitoes are repelled from the surface. The insecticidal properties required a much higher concentration of 2. All tests were conducted by forcing mosquitoes (5 per replicate×5 replicates) into contact with treated muslin cloth. The number of knocked down (KD) (moribund or dead) were counted after specific time intervals (15 min, 1 h, 5 h, and 8 h). For rapid KD in 15 min, a dose of 30 mg/cm$^2$ or greater is needed.

The true comparison of insecticidal activity compared to repellent activity should be done using a "touch test" where mosquitoes are placed only briefly into contact with a treated surface then held for observation in some cases up to 48 h. Clearly, a touch exposure would transfer a significantly less quantity of chemical to an insect and therefore require a much higher concentration than 30 mg/cm$^2$ to produce insecticidal activity.

Thus we have shown that the chromene analogs synthesized based on the natural chromene amide, particularly 2 and 11, surprisingly act as mosquito repellents, especially since they exhibited significantly higher duration of protection and higher activity than DEET. All of the references cited herein, including U.S. patents, are incorporated by reference in their entirety. Also incorporated by reference in their entirety are the following references: Kitchen, Lynn W., et al., Journal of vector ecology: journal of the Society for Vector Ecology, 34(1): 50-61(2009); U.S. patent application Ser. No. 11/953,343 filed 11 Dec. 2007; U.S. patent application Ser. No. 12/141,511 filed 18 Jun. 2008.

Thus, in view of the above, the present invention concerns (in part) the following:

A composition comprising (or consisting essentially of or consisting of) at least one member of the group consisting of where (2) R$_1$=CH$_2$OH and R$_2$, R$_3$, R$_4$=H; (3) where R$_1$=OH and R$_2$=C(O)CH$_3$ and R$_3$, R$_4$=H; (4) where R$_1$=OMe, R$_2$ and R$_3$=H, and R$_4$=CH$_2$OH; (5) where R$_1$, R$_3$, and R$_4$=H and R$_2$=C(O)OCH$_3$; (6) where R$_2$, R$_3$, and R$_4$=H and R$_1$=C(O)OCH$_3$; (7) where R$_1$, R$_3$, and R$_4$=H and R$_2$=CH$_2$OH; (8) where R$_1$, R$_2$, and R$_4$=H and R$_3$=C(O)

$OCH_3$; (9) where $R_2=CH_2CH_2OH$ and $R_1$, $R_3$, and $R_4=H$; (10) where $R_2=CH_2C(O)OCH_3$ and $R_1$, $R_3$, and $R_4=H$; (11) where $R_1=CH_2OH$, $R_2$ and $R_3=H$, and $R_4=Cl$; (12) where $R_1$, $R_2$, and $R_4=H$ and $R_3=Cl$; (13) where $R_1=COOH$, $R_2$ and $R_3=H$, and $R_4=Cl$; (14) where $R_1=C(O)OCH_3$, $R_2$ and $R_3=H$, and $R_4=Cl$; (15) where $R_1$, $R_2$ and $R_3=H$ and $R_4=Cl$; (16) where $R_1=C(O)OCH_3$, $R_3$ and $R_4=H$, and $R_2=Cl$; (17) where $R_1$, $R_3$ and $R_4=H$ and $R_2=Cl$; (18) where $R_1=CH_2OCH_3$, $R_2$, $R_3$ and $R_4=H$; (19) where $R_2=CH_2CH_2OCH_3$ and $R_1$, $R_3$ and $R_4=H$; and mixtures thereof, and optionally a carrier or carrier material.

The above composition, including $R_1=CH_2OH$ and $R_2$, $R_3$, $R_4=H$. The above composition, not including $R_1=CH_2OH$ and $R_2$, $R_3$, $R_4=H$. The above composition, including $R_1=OH$ and $R_2=C(O)CH_3$ and $R_3$, $R_4=H$. The above composition, not including $R_1=OH$ and $R_2=C(O)CH_3$ and $R_3$, $R_4=H$. The above composition, including $R_1=OMe$, $R_2$ and $R_3=H$, and $R_4=CH_2OH$. The above composition, not including $R_1=OMe$, $R_2$ and $R_3=H$, and $R_4=CH_2OH$. The above composition, including $R_1$, $R_3$, and $R_4=H$ and $R_2=C(O)OCH_3$. The above composition, not including $R_1$, $R_3$, and $R_4=H$ and $R_2=C(O)OCH_3$. The above composition, including $R_2$, $R_3$, and $R_4=H$ and $R_1=C(O)OCH_3$. The above composition, not including $R_2$, $R_3$, and $R_4=H$ and $R_1=C(O)OCH_3$. The above composition, including $R_1$, $R_3$, and $R_4=H$ and $R_2=CH_2OH$. The above composition, not including $R_1$, $R_3$, and $R_4=H$ and $R_2=CH_2OH$. The above composition, including $R_1$, $R_2$, and $R_4=H$ and $R_3=C(O)OCH_3$. The above composition, not including $R_1$, $R_2$, and $R_4=H$ and $R_3=C(O)OCH_3$. The above composition, including $R_2=CH_2CH_2OH$ and $R_1$, $R_3$, and $R_4=H$. The above composition, not including $R_2=CH_2CH_2OH$ and $R_1$, $R_3$, and $R_4=H$. The above composition, including $R_2=CH_2C(O)OCH_3$ and $R_1$, $R_3$, and $R_4=H$. The above composition, not including $R_2=CH_2C(O)OCH_3$ and $R_1$, $R_3$, and $R_4=H$. The above composition, including $R_1=CH_2OH$, $R_2$ and $R_3=H$, and $R_4=Cl$. The above composition, not including $R_1=CH_2OH$, $R_2$ and $R_3=H$, and $R_4=Cl$. The above composition, including $R_1$, $R_2$, and $R_4=H$ and $R_3=Cl$. The above composition, not including $R_1$, $R_2$, and $R_4=H$ and $R_3=Cl$. The above composition, including $R_1=COOH$, $R_2$ and $R_3=H$, and $R_4=Cl$. The above composition, not including $R_1=COOH$, $R_2$ and $R_3=H$, and $R_4=Cl$. The above composition, including $R_1=C(O)OCH_3$, $R_2$ and $R_3=H$, and $R_4=Cl$. The above composition, not including $R_1=C(O)OCH_3$, $R_2$ and $R_3=H$, and $R_4=Cl$. The above composition, including $R_1$, $R_2$ and $R_3=H$ and $R_4=Cl$. The above composition, not including $R_1$, $R_2$ and $R_3=H$ and $R_4=Cl$. The above composition, including $R_1=C(O)OCH_3$, $R_3$ and $R_4=H$, and $R_2=Cl$. The above composition, not including $R_1=C(O)OCH_3$, $R_3$ and $R_4=H$, and $R_2=Cl$. The above composition, including $R_1$, $R_3$ and $R_4=H$ and $R_2=Cl$. The above composition, not including $R_1$, $R_3$ and $R_4=H$ and $R_2=Cl$. The above composition, including $R_1=CH_2OCH_3$, $R_2$, $R_3$ and $R_4=H$. The above composition, not including $R_1=CH_2OCH_3$, $R_2$, $R_3$ and $R_4=H$. The above composition, including $R_2=CH_2CH_2OCH_3$ and $R_1$, $R_3$ and $R_4=H$. The above composition, not including $R_2=CH_2CH_2OCH_3$ and $R_1$, $R_3$ and $R_4=H$.

The above composition, comprising (or consisting essentially of or consisting of) at least two members of the group consisting of where (2) $R_1=CH_2OH$ and $R_2$, $R_3$, $R_4=H$; (3) where $R_1=OH$ and $R_2=C(O)CH_3$ and $R_3$, $R_4=H$; (4) where $R_1=OMe$, $R_2$ and $R_3=H$, and $R_4=CH_2OH$; (5) where $R_1$, $R_3$, and $R_4=H$ and $R_2=C(O)OCH_3$; (6) where $R_2$, $R_3$, and $R_4=H$ and $R_1=C(O)OCH_3$; (7) where $R_1$, $R_3$, and $R_4=H$ and $R_2=CH_2OH$; (8) where $R_1$, $R_2$, and $R_4=H$ and $R_3=C(O)OCH_3$; (9) where $R_2=CH_2CH_2OH$ and $R_1$, $R_3$, and $R_4=H$; (10) where $R_2=CH_2C(O)OCH_3$ and $R_1$, $R_3$, and $R_4=H$; (11) where $R_1=CH_2OH$, $R_2$ and $R_3=H$, and $R_4=Cl$; (12) where $R_1$, $R_2$, and $R_4=H$ and $R_3=Cl$; (13) where $R_1=COOH$, $R_2$ and $R_3=H$, and $R_4=Cl$; (14) where $R_1=C(O)OCH_3$, $R_2$ and $R_3=H$, and $R_4=Cl$; (15) where $R_1$, $R_2$ and $R_3=H$ and $R_4=Cl$; (16) where $R_1=C(O)OCH_3$, $R_3$ and $R_4=H$, and $R_2=Cl$; (17) where $R_1$, $R_3$ and $R_4=H$ and $R_2=Cl$; (18) where $R_1=CH_2CH_3$, $R_2$, $R_3$ and $R_4=H$; (19) where $R_2=CH_2CH_2OCH_3$ and $R_1$, $R_3$ and $R_4=H$; and mixtures thereof, and optionally a carrier or carrier material.

A method for repelling blood-sucking and biting insects, ticks and mites, said method comprising (or consisting essentially of or consisting of) treating an object or area with a composition comprising a blood-sucking and biting insects, ticks and mites repelling effective amount of at least one compound selected from the group consisting of where (2) $R_1=CH_2OH$ and $R_2$, $R_3$, $R_4=H$; (3) where $R_1=OH$ and $R_2=C(O)CH_3$ and $R_3$, $R_4=H$; (4) where $R_1=OMe$, $R_2$ and $R_3=H$, and $R_4=CH_2OH$; (5) where $R_1$, $R_3$, and $R_4=H$ and $R_2=C(O)OCH_3$; (6) where $R_2$, $R_3$, and $R_4=H$ and $R_1=C(O)OCH_3$; (7) where $R_1$, $R_3$, and $R_4=H$ and $R_2=CH_2OH$; (8) where $R_1$, $R_2$, and $R_4=H$ and $R_3=C(O)OCH_3$; (9) where $R_2=CH_2CH_2OH$ and $R_1$, $R_3$, and $R_4=H$;

(10) where $R_2=CH_2C(O)OCH_3$ and $R_1$, $R_3$, and $R_4=H$; (11) where $R_1=CH_2OH$, $R_2$ and $R_3=H$, and $R_4=Cl$; (12) where $R_1$, $R_2$, and $R_4=H$ and $R_3=Cl$; (13) where $R_1=COOH$, $R_2$ and $R_3=H$, and $R_4=Cl$; (14) where $R_1=C(O)OCH_3$, $R_2$ and $R_3=H$, and $R_4=Cl$; (15) where $R_1$, $R_2$ and $R_3=H$ and $R_4=Cl$; (16) where $R_1=C(O)OCH_3$, $R_3$ and $R_4=H$, and $R_2=Cl$; (17) where $R_1$, $R_3$ and $R_4=H$ and $R_2=Cl$; (18) where $R_1=CH_2OCH_3$, $R_2$, $R_3$ and $R_4=H$; (19) where $R_2=CH_2CH_2OCH_3$ and $R_1$, $R_3$ and $R_4=H$; and mixtures thereof, and optionally a carrier or carrier material. The term "effective amount," as used herein, also means an amount which does not kill blood-sucking and biting insects, ticks and mites.

The above method, comprising (or consisting essentially of or consisting of) treating an object or area with a composition comprising a blood-sucking and biting insects, ticks and mites repelling effective amount of at least two compounds selected from the group consisting of where (2) $R_1=CH_2OH$ and $R_2$, $R_3$, $R_4=H$; (3) where $R_1=OH$ and $R_2=C(O)CH_3$ and $R_3$, $R_4=H$; (4) where $R_1=OMe$, $R_2$ and $R_3=H$, and $R_4=CH_2OH$; (5) where $R_1$, $R_3$, and $R_4=H$ and $R_2=C(O)OCH_3$; (6) where $R_1$, $R_3$, and $R_4=H$ and $R_1=C(O)OCH_3$, (7) where $R_1$, $R_3$, and $R_4=H$ and $R_2=CH_2OH$; (8) where $R_1$, $R_2$, and $R_4=H$ and $R_3=C(O)OCH_3$; (9) where $R_2=CH_2CH_2OH$ and $R_1$, $R_3$, and $R_4=H$; (10) where $R_2=CH_2C(O)OCH_3$ and $R_1$, $R_3$, and $R_4=H$; (11) where $R_1=CH_2OH$, $R_2$ and $R_3=H$, and $R_4=Cl$; (12) where $R_1$, $R_2$, and $R_4=H$ and $R_3=Cl$; (13) where $R_1=COOH$, $R_2$ and $R_3=H$, and $R_4=Cl$; (14) where $R_1=C(O)OCH_3$, $R_2$ and $R_3=H$, and $R_4=Cl$; (15) where $R_1$, $R_2$ and $R_3=H$ and $R_4=Cl$; (16) where $R_1=C(O)OCH_3$, $R_3$ and $R_4=H$, and $R_2=Cl$; (17) where $R_1$, $R_3$ and $R_4=H$ and $R_2=Cl$; (18) where $R_1=CH_2OCH_3$, $R_2$, $R_3$ and $R_4=H$; (19) where $R_2=CH_2CH_2OCH_3$ and $R_1$, $R_3$ and $R_4=H$; and mixtures thereof, and optionally a carrier or carrier material.

The above method, wherein said composition comprises at least one compound selected from the group consisting of where (2) $R_1=CH_2OH$ and $R_2$, $R_3$, $R_4=H$; (11) where $R_3=CH_2OH$, $R_2$ and $R_3=H$, and $R_4=Cl$; and mixtures thereof, and optionally a carrier or carrier material.

The above method, wherein (2) $R_1=CH_2OH$ and $R_2$, $R_3$, $R_4=H$.

The above method, wherein (11) where $R_1=CH_2OH$, $R_2$ and $R_3=H$, and $R_4=Cl$.

The above method, wherein said compound has $R_1=CH_2OH$ and $R_2$, $R_3$, $R_4=H$. The above method, wherein said compound does not have $R_1=CH_2OH$ and $R_2$, $R_3$, $R_4=H$. The above method, wherein said compound has $R_1=OH$ and $R_2=C(O)CH_3$ and $R_3$, $R_4=H$. The above method, wherein said compound does not have $R_1=OH$ and $R_2=C(O)CH_3$ and $R_3$, $R_4=H$. The above method, wherein said compound has $R_1=OMe$, $R_2$ and $R_3=H$, and $R_4=CH_2OH$. The above method, wherein said compound does not have $R_1=OMe$, $R_2$ and $R_3=H$, and $R_4=CH_2OH$. The above method, wherein said compound has $R_1$, $R_3$, and $R_4=H$ and $R_2=C(O)OCH_3$. The above method, wherein said compound does not have $R_1$, $R_3$, and $R_4=H$ and $R_2=C(O)OCH_3$. The above method, wherein said compound has $R_2$, $R_3$, and $R_4=H$ and $R_1=C(O)OCH_3$. The above method, wherein said compound does not have $R_2$, $R_3$, and $R_4=H$ and $R_1=C(O)OCH_3$. The above method, wherein said compound has $R_1$, $R_3$, and $R_4=H$ and $R_2=CH_2OH$. The above method, wherein said compound does not have $R_1$, $R_3$, and $R_4=H$ and $R_2=CH_2OH$. The above method, wherein said compound has $R_1$, $R_2$, and $R_4=H$ and $R_3=C(O)OCH_3$. The above method, wherein said compound does not have $R_1$, $R_2$, and $R_4=H$ and $R_3=C(O)OCH_3$. The above method, wherein said compound has $R_2=CH_2CH_2OH$ and $R_1$, $R_3$, and $R_4=H$. The above method, wherein said compound does not have $R_2=CH_2CH_2OH$ and $R_1$, $R_3$, and $R_4=H$. The above method, wherein said compound has $R_2=CH_2C(O)OCH_3$ and $R_1$, $R_3$, and $R_4=H$. The above method, wherein said compound does not have $R_2=CH_2C(O)OCH_3$ and $R_1$, $R_3$, and $R_4=H$. The above method, wherein said compound has $R_1=CH_2OH$, $R_2$ and $R_3=H$, and $R_4=Cl$. The above method, wherein said compound does not have $R_1=CH_2OH$, $R_2$ and $R_3=H$, and $R_4=Cl$. The above method, wherein said compound has $R_1$, $R_2$, and $R_4=H$ and $R_3=Cl$. The above method, wherein said compound does not have $R_1$, $R_2$, and $R_4=H$ and $R_3=Cl$. The above method, wherein said compound has $R_1=COOH$, $R_2$ and $R_3=H$, and $R_4=Cl$. The above method, wherein said compound does not have $R_1=COOH$, $R_2$ and $R_3=H$, and $R_4=Cl$. The above method, wherein said compound has $R_1=C(O)OCH_3$, $R_2$ and $R_3=H$, and $R_4=Cl$. The above method, wherein said compound does not have $R_1=C(O)OCH_3$, $R_2$ and $R_3=H$, and $R_4=Cl$. The above method, wherein said compound has $R_1$, $R_2$ and $R_3=H$ and $R_4=Cl$. The above method, wherein said compound does not have $R_1$, $R_2$ and $R_3=H$ and $R_4=Cl$. The above method, wherein said compound has $R_1=C(O)OCH_3$, $R_3$ and $R_4=H$, and $R_2=Cl$. The above method, wherein said compound does not have $R_1=C(O)OCH_3$, $R_3$ and $R_4=H$, and $R_2=Cl$. The above method, wherein said compound has $R_1$, $R_3$ and $R_4=H$ and $R_2=Cl$. The above method, wherein said compound does not have $R_1$, $R_3$ and $R_4=H$ and $R_2=Cl$. The above method, wherein said compound has $R_1=CH_2OCH_3$, $R_2$, $R_3$ and $R_4=H$. The above method, wherein said compound does not have $R_1=CH_2OCH_3$, $R_2$, $R_3$ and $R_4=H$. The above method, wherein said compound has $R_2=CH_2CH_2OCH_3$ and $R_1$, $R_3$ and $R_4=H$. The above method, wherein said compound does not have $R_2=CH_2CH_2OCH_3$ and $R_1$, $R_3$ and $R_4=H$.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims

TABLE 1

Ae. aegypti Minimum Effective Dosage (mg/cm$^2$)

| Compound | M4 | M5 | M8 | M9 | M10 | Average | Std. Dev. |
|---|---|---|---|---|---|---|---|
| 3 | >1.500 | 0.187 | >1.500 | >1.500 | >1.500 | N/A | — |
| 4 | >1.500 | 0.375 | 0.375 | 0.750 | >1.500 | N/A | — |
| 5 | >1.500 | 0.375 | 0.187 | 0.375 | >1.500 | N/A | — |
| 2 | 0.011 | 0.011 | 0.011 | 0.094 | 0.047 | 0.035 | 0.037 |
| DEET | 0.111 | 0.023 | 0.023 | 0.023 | 0.023 | 0.021 | 0.005 |
| Acetone Control | NR | NR | NR | NR | NR | N/A | — |

Human subject raw data by coded identifier (M4, M5, M8, M9, M10)
NR = Not repellent,
N/A = not applicable due to no repellency at highest concentration for some or all volunteers.

TABLE 2

Ae. aegypti Minimum Effective Dosage (mg/cm$^2$)

|  | M1 | F1 | M2 | Average | Std. Dev. |
|---|---|---|---|---|---|
| 10 | 0.750 | 0.375 | 0.375 | 0.500 | 0.217 |
| 9 | 0.375 | 0.375 | 0.375 | 0.375 | 0.000 |
| 16 | >1.500 | >1.500 | >1.500 | N/A | N/A |
| 14 | >1.500 | >1.500 | >1.500 | N/A | N/A |
| 11 | 0.011 | 0.011 | 0.011 | 0.011 | 0.000 |
| 13 | >1.500 | >1.500 | >1.500 | N/A | N/A |
| 12 | 0.750 | 0.750 | 0.750 | 0.750 | 0.000 |
| 15 | 0.094 | 0.094 | 0.187 | 0.125 | 0.054 |
| 2 | 0.023 | 0.023 | 0.023 | 0.023 | 0.000 |

Human subjects raw data by coded identifier (M1, F1, M2)
N/A = not applicable due to no repellency at highest concentration for some or all volunteers.

TABLE 3

Duration of protection against Ae. aegypti in days

|  | Dosage (mg/cm$^2$) | M-3 Days Protection | Proportion to DEET |
|---|---|---|---|
| 9 | 0.75 | 1 | 0.50 |
| 11 | 0.75 | 7 | 1.00 |
| 13 | 0.75 | 1 | 0.50 |
| 17 | 0.75 | 1 | 0.50 |
| 2 | 0.75 | 6 | 3.00 |
| DEET | 0.75 | 2 | 1.00 |

TABLE 4

An. albimanus Minimum Effective Dosage (mg/cm$^2$)

|  | M4 | M5 | M8 | M9 | M10 | Average | Std. Dev. |
|---|---|---|---|---|---|---|---|
| 3 | 0.094 | >1.500 | >1.500 | 0.375 | >1.500 | N/A | — |
| 4 | >1.500 | >1.500 | >1.500 | 0.750 | >1.500 | N/A | — |
| 5 | 0.187 | 0.375 | >1.500 | 0.187 | 0.750 | N/A | — |
| 2 | 0.047 | 0.375 | 0.187 | 0.375 | 0.187 | 0.234 | 0.141 |
| DEET | 0.011 | 0.047 | 0.023 | 0.023 | 0.023 | 0.025 | 0.013 |
| Acetone Control | NR | NR | NR | NR | NR | N/A | — |

NR = not repellent,
N/A = Not applicable

TABLE 5

Ae. aegypti Minimum Effective Dosage (mg/cm$^2$)

|  | M4 | M5 | M8 | Average | Std. Dev. | Highest Dose (mg/cm2) |
|---|---|---|---|---|---|---|
| 10 | >0.375 | >0.375 | >0.375 | N/A | — | 0.375 |
| 7 | >0.187 | >0.187 | >0.187 | N/A | — | 0.187 |
| 6 | >0.375 | >0.375 | >0.375 | N/A | — | 0.375 |
| 8 | >0.375 | >0.375 | >0.375 | N/A | — | 0.375 |
| 2 | 0.011 | 0.011 | 0.006 | 0.009 | 0.003 | 0.375 |
| 18 | 0.047 | 0.047 | 0.187 | 0.094 | 0.081 | 0.375 |
| 19 | >0.375 | >0.375 | >0.375 | N/A | — | 0.375 |
| DEET | 0.011 | 0.011 | 0.023 | 0.015 | 0.007 | 0.375 |

N/A = compound ineffective at highest available dose

TABLE 6

MED values of varying molar ratios of 2 and DEET

Ae. aegypti Minimum Effective Dosage (mg/cm$^2$)

| Molar ratio 2:DEET | M4 | M5 | M8 | Average | Std. Dev. | Highest Dose (mg/cm2) |
|---|---|---|---|---|---|---|
| 1:0 | 0.0156 | 0.0313 | 0.0313 | 0.0260 | 0.009 | 4.0 |
| 1:1 | 0.0156 | 0.0156 | 0.0313 | 0.0208 | 0.009 | 4.0 |
| 1:2 | 0.0313 | 0.0313 | 0.0313 | 0.0313 | 0.000 | 4.0 |
| 1:3 | 0.0156 | 0.0313 | 0.0156 | 0.0208 | 0.009 | 4.0 |
| 1:4 | 0.0313 | 0.0313 | 0.0156 | 0.0260 | 0.009 | 4.0 |
| 1:5 | 0.0313 | 0.0313 | 0.0156 | 0.0260 | 0.009 | 4.0 |
| 1:6 | 0.0156 | 0.0156 | 0.0156 | 0.0156 | 0.000 | 4.0 |
| 1:7 | 0.0313 | 0.0156 | 0.0156 | 0.0208 | 0.009 | 4.0 |
| 1:8 | 0.0156 | 0.0156 | 0.0156 | 0.0156 | 0.000 | 4.0 |
| 2:1 | 0.0313 | 0.0313 | 0.0156 | 0.0260 | 0.009 | 4.0 |
| 3:1 | 0.0156 | 0.0313 | 0.0156 | 0.0208 | 0 009 | 4.0 |
| 4:1 | 0.0078 | 0.0313 | 0.0156 | 0.0182 | 0.012 | 4.0 |
| 5:1 | 0.0156 | 0.0313 | 0.0156 | 0.0208 | 0.009 | 4.0 |
| 6:1 | 0.0313 | 0.0313 | 0.0313 | 0.0313 | 0.000 | 4.0 |
| 7:1 | 0.0156 | 0.0313 | 0.0313 | 0.0260 | 0.009 | 4.0 |
| 8:1 | 0.0156 | 0.0313 | 0.0313 | 0.0260 | 0.009 | 4.0 |
| 0:1 | 0.0313 | 0.0313 | 0.0313 | 0.0313 | 0.000 | 4.0 | n/a = compound ineffective at highest available dose

TABLE 7

Surface concentration exposure of female Aedes aegypti to cloth treated with 2

| Effect on Aedes aegypti mosquitoes | Sufrace Concentration of 2 (mg/cm$^2$) |
|---|---|
| MED for ~100% Repellency (ED99) | 0.011 |
| KD$_{100}$ @ 8 h (2 min forced exposure) | 0.96 |
| KD$_{100}$ @ 5 h (2 min forced exposure) | 7.69 |
| KD$_{100}$ @ 1 h (2 min forced exposure) | 15.38 |
| KD$_{100}$ @ 15 m (2 min forced exposure) | 30.76 |

We claim:

1. A method for repelling blood-sucking and biting insects, ticks and mites, said method comprising treating an object or area with a composition comprising an effective amount of at least one compound selected from the group consisting of

(1)

or where $R_1$=CH$_2$OH and $R_2$, $R_3$, $R_4$=H; where $R_1$=OH and $R_2$=C(O)CH$_3$ and $R_3$, $R_4$=H; where $R_1$=OMe, $R_2$ and $R_3$=H, and $R_4$=CH$_2$OH; where $R_1$, $R_3$, and $R_4$=H and $R_2$=C(O)OCH$_3$; where $R_2$, $R_3$, and $R_4$=H and $R_1$=C(O)OCH$_3$; where $R_1$, $R_3$, and $R_4$=H and $R_2$=CH$_2$OH; where $R_1$, $R_2$, and $R_4$=H and $R_1$=C(O)OCH$_3$; where $R_2$=CH$_2$CH$_2$OH and $R_1$, $R_3$, and $R_4$=H; where $R_2$=CH$_2$C(O)OCH$_3$ and $R_1$, $R_3$, and $R_4$=H; where $R_1$=CH$_2$OH, $R_2$ and $R_3$=H, and $R_4$=Cl; where $R_1$, $R_2$, and $R_4$=H and $R_3$=Cl; where $R_1$=COOH, $R_2$ and $R_3$=H, and $R_4$=Cl; where $R_1$=C(O)OCH$_3$, $R_2$ and $R_3$H, and $R_4$Cl; where $R_1$, $R_2$ and $R_3$=H and $R_4$=Cl; where $R_1$=C(O)OCH$_3$, $R_3$ and $R_4$=H, and $R_2$=Cl; where $R_1$, $R_3$ and $R_4$=H and $R_2$=Cl; where $R_1$=CH$_2$OCH$_3$, $R_2$, $R_3$ and $R_4$=H; where $R_2$=CH$_2$CH$_2$OCH$_3$ and $R_1$, $R_3$ and $R_4$=H; and mixtures thereof, and optionally a carrier or carrier material.

2. The method according to claim 1, wherein said composition comprises at least one compound selected from the group consisting of where $R_1$=CH$_2$OH and $R_2$, $R_3$, $R_4$=H; where $R_1$=CH$_2$OH, $R_2$ and $R_3$=H, and $R_4$=Cl; and mixtures thereof, and optionally a carrier or carrier material.

3. The method according to claim 1, wherein $R_1$=CH$_2$OH and $R_2$, $R_3$, $R_4$=H.

4. The method according to claim 1, wherein where $R_1$=CH$_2$OH, $R_2$ and $R_3$=H, and $R_4$=Cl.

* * * * *